(12) United States Patent
Shen et al.

(10) Patent No.: US 11,099,252 B2
(45) Date of Patent: Aug. 24, 2021

(54) MAGNETIC RESONANCE IMAGING METHOD

(71) Applicant: SHANGHAI UNITED IMAGING HEALTHCARE CO., LTD., Shanghai (CN)

(72) Inventors: Baozhong Shen, Guangdong (CN); Weiguo Zhang, Guangdong (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 1044 days.

(21) Appl. No.: 15/541,167

(22) PCT Filed: Oct. 9, 2015

(86) PCT No.: PCT/CN2015/091525
§ 371 (c)(1),
(2) Date: Nov. 3, 2017

(87) PCT Pub. No.: WO2016/074544
PCT Pub. Date: May 19, 2016

(65) Prior Publication Data
US 2018/0059200 A1    Mar. 1, 2018

(30) Foreign Application Priority Data
Nov. 12, 2014    (CN) .......................... 201410635767.1

(51) Int. Cl.
*G01R 33/56*    (2006.01)
*A61B 5/055*    (2006.01)
(Continued)

(52) U.S. Cl.
CPC .......... *G01R 33/5602* (2013.01); *A61B 5/055* (2013.01); *A61B 5/7257* (2013.01); *G01R 33/565* (2013.01); *A61B 2576/023* (2013.01)

(58) Field of Classification Search
CPC .. A61B 5/055; A61B 5/7257; G01R 33/5602; G01R 33/565; G01R 33/56
See application file for complete search history.

(56) References Cited

U.S. PATENT DOCUMENTS

2001/0027262 A1* 10/2001 Mistretta ............ G01R 33/4824
600/9
2002/0107438 A1* 8/2002 Liu ..................... G01R 33/5601
600/410
(Continued)

FOREIGN PATENT DOCUMENTS

CN    1116078 A    2/1996
CN    103845055 A    6/2014
(Continued)

OTHER PUBLICATIONS

Borrello et al., "Regional Phase Correction of Inversion-Recovery MR Images". Magnetic Resonance in Medicine 14, 56-67 (1990). (Year: 1990).*

(Continued)

*Primary Examiner* — Yi-Shan Yang
(74) *Attorney, Agent, or Firm* — Metis IP LLC

(57) ABSTRACT

The method for magnetic resonance imaging described in the present disclosure may include generating an inversion recovery image by scanning an object using an inversion recovery sequence. The method may also include generating a real part image corresponding to the inversion recovery image by processing the inversion recovery image. The method may also include obtaining a signal line of a reference image without inversion recovery, the reference image corresponding to the real part image. The method may also include determining a phase-corrected signal line of the reference image by performing a phase correction on the signal line of the reference image. The method may also (Continued)

include determining a polarity of the real part image based on the phase-corrected signal line of the reference image.

15 Claims, 5 Drawing Sheets

(51) Int. Cl.
  *G01R 33/565* (2006.01)
  *A61B 5/00* (2006.01)

(56) References Cited

U.S. PATENT DOCUMENTS

| | | | | |
|---|---|---|---|---|
| 2010/0134107 A1* | 6/2010 | Kitamoto | ............ | G01R 33/565 324/309 |
| 2012/0161760 A1 | 6/2012 | Kuhara | | |
| 2013/0272591 A1 | 10/2013 | Xue et al. | | |
| 2015/0131884 A1* | 5/2015 | Kimura | ................ | A61B 5/0263 382/131 |
| 2015/0316631 A1* | 11/2015 | Ma | .................... | G01R 33/5611 324/309 |
| 2015/0355303 A1* | 12/2015 | Kuhara | ............. | G01R 33/5611 324/322 |
| 2016/0169999 A1* | 6/2016 | Herza | .................. | G01R 33/563 600/411 |

FOREIGN PATENT DOCUMENTS

| | | | |
|---|---|---|---|
| JP | 2001299724 A | * | 10/2001 |
| JP | 2001299724 A | | 10/2001 |
| WO | 2012151551 A2 | | 11/2012 |

OTHER PUBLICATIONS

International Search Report in PCT/CN2015/091525 dated Dec. 30, 2015, 2 pages.

Written Opinion in PCT/CN2015/091525 dated Dec. 30, 2015, 5 pages.

* cited by examiner

MAGNETIC RESONANCE IMAGING METHOD

CROSS-REFERENCE TO RELATED APPLICATIONS

This present application claims priority of Chinese Patent Application No. 201410635767.1 filed on Nov. 12, 2014, the entire contents of which are hereby incorporated by reference.

TECHNICAL FIELD

The present disclosure generally relates to magnetic resonance imaging, and more particularly, to methods for magnetic resonance imaging.

BACKGROUND

In the magnetic resonance imaging (MRI) technology, when a radio frequency (RF) pulse with a frequency that is the same as a procession frequency of protons is applied on processional protons in a main magnetic field, the protons may resonate. On the microscopic level, protons with a low energy level may absorb energy and jump to a high energy level. On the macroscopic level, the magnetization vectors of the protons may deflect. The deflection angle of the macroscopic magnetization vector may vary with the energy of the RF pulse. The higher the energy of the RF pulse is, the larger the deflection angle of the macroscopic magnetization vector may be. An RF pulse that may cause a macroscopic magnetization vector to deflect by a certain angle may be referred to as a certain angle pulse, such as a 90° pulse, a small angle pulse (e.g., the certain angle is less than 90°), a 180° pulse, etc. In turn, the larger the deflection angle of the macroscopic magnetization vector is, the higher the energy that the protons in an excited tissue absorb may be, the higher the energy that the protons need to release may be after the RF pulse is no longer applied to the processional protons, and the longer the longitudinal relaxation time of the excited tissue may be.

When a tissue is excited by a 180° RF pulse, the macroscopic longitudinal relaxation vector of the tissue may deflect by 180°, which indicates that the macroscopic longitudinal relaxation vector of the tissue may deflect to a direction opposite to the main magnetic field. The 180° RF pulse may also be referred to as an inversion pulse. Because the energy of the 180° RF pulse is twice the energy of a 90° RF pulse, the recovery time that the longitudinal magnetization vector deflected by 180° needs to completely recover to the original state may also prolong. In prior art, a sequence including a 180° inversion pulse may be referred to as an inversion recovery (IR) sequence.

In an IR sequence, recovery times of longitudinal magnetization vectors of different tissues may vary with an inversion time TI. As shown in FIG. 1, the solid line refers to a recovery curve of tissue A. The dash line refers to a recovery curve of tissue B. The intersection of a recovery curve and the X axis may be referred to as the inversion time TI. The inversion time TI of tissue A is 390 microseconds. The inversion time TI of tissue B is 770 microseconds. When the inversion time TI is equal to 500 ms, polarities of signals collected from tissue A and tissue B may be different. As shown in FIG. 1, the polarity of signals collected from tissue A is positive at the inversion time TI of 500 microseconds and the polarity of signals collected from tissue B is negative at the inversion time TI of 500 microseconds. In image reconstruction, polarities of signals collected from different tissues need to be consistent with the actual polarities of the tissues in order to ensure contrast consistency. The contrast consistency may indicate that tissue A may be brighter than tissue B in an image if the polarity of signals collected from tissue A is positive and the polarity of signals collected from tissue B is negative.

However, in the real part imaging based on the IR sequence, the absolute value of the intensity of signals collected from tissue B at the inversion time of 500 microseconds may be greater than the absolute value of the intensity of signals collected from tissue A at the inversion time of 500 microseconds, and tissue B may be brighter than tissue A in an image, which may lead to contrast inconsistency in the image. In prior art, a solution is proposed as follows:

An inversion recovery (IR) image may be represented by an equation of $S(x,y)=I(x,y)e^{j(\varphi_i(x,y)+\varphi_e(x,y))}$. As used herein, x refers to a position of a pixel in the IR image along the readout (RO) direction; y refers to a position of the pixel along the phase encoding direction; I(x,y) refers to the amplitude of the pixel; $\varphi_i(x,y)$ refers to a polarity phase (e.g., 0 or pi) of the pixel; and $\varphi_e(x,y)$ refers to an error phase of the pixel. For real part imaging without a pre-scan, a phase correction may be performed on the inversion recovery (IR) image. Before the ambiguity in polarity is eliminated, the phase-corrected IR image may be represented as: $\hat{S}(x,y)=I(x,y)e^{j\varphi_i(x,y)}$ or $\hat{S}(x,y)=-I(x,y)e^{j\varphi_i(x,y)}$.

Method 1: a sign of a sum of real parts in a real part image may be determined based on an inversion time TI. In Method 1, an inversion time threshold $TI_0$ may be determined. When TI is less than $TI_0$, the sum of the real parts in the real part image may be determined to be negative. When TI is larger than $TI_0$, the sum of the real parts in the real part image may be determined to be positive. The sign of the sum of the real parts in the real part image may be determined according to the equation below:

$$\sum_{(x,y)} \hat{S}_m(x,y) \begin{cases} < 0, \text{ if } TI < TI_0 \\ > 0, \text{ if } TI > TI_0 \end{cases},$$

where m refers to the slice number of a scan slice. If the result determined based on the generated real part image does not satisfy the above equation, the polarity of the real part image may be inversed.

A problem of Method 1 is that it is hard to determine a steady and commonly applicable inversion time threshold $TI_0$. On the one hand, due to individual differences and differences among different scan slices, a sum of the signals collected from different tissues (e.g., cerebrospinal fluid, gray matter, etc.) may be different. It is hard to eliminate the ambiguity in polarity using Method 1. On the other hand, the inversion time TI of different tissues may be different, which makes Method 1 difficult to apply to all tissues.

Method 2: a "Moment of Inertia" of an image may be determined based on the distribution characteristic of signals. For a real part image of a brain, the "Moment of Inertia" of the image whose center of gravity is the origin may be determined based on the equation below:

$$MI = \Sigma_m \Sigma_{(x,y)} \hat{S}_m(x,y)(x^2+y^2),$$

where $\hat{S}_m(x,y)$ refers to a real part image of the $m^{th}$ slice before the ambiguity in polarity is eliminated. Because cerebrospinal fluid and gray matter whose polarities are generally negative may be mainly in the center area of the brain, while scalp fat whose polarity is generally positive may be mainly in the periphery area of the brain, the Moment of Inertia may be positive when the polarity of the real part image is correct, and the Moment of Inertia may be negative when the polarity of the real part image is incorrect. Method 2 is applicable only to the real part imaging of a brain and needs the inversion time to be greater than an inversion time threshold such that the scalp fat show sufficiently strong positive signals. However, the inversion time threshold may vary with different individuals and different scan positions, which makes Method 2 hard to be widely used.

In summary, it is desired to provide methods for MRI to better determine polarities of signals collected from tissue.

SUMMARY

In the magnetic resonance imaging (MRI) technology using an inversion recovery (IR) sequence, in order to solve a problem relating to inaccuracy determination of signal polarities of different tissues in a real part image, a method for magnetic resonance imaging is provided according to a first aspect of the present disclosure. The method may include generating an inversion recovery image by scanning an object using an inversion recovery sequence. The method may also include generating a real part image corresponding to the inversion recovery image by processing the inversion recovery image. The method may also include obtaining a signal line of a reference image without inversion recovery, the reference image corresponding to the real part image. The method may also include determining a phase-corrected signal line of the reference image by performing a phase correction on the signal line of the reference image. The method may also include determining a polarity of the real part image based on the phase-corrected signal line of the reference image.

In some embodiments, the signal line of the reference image without inversion recovery may be determined before or after the real part image is generated.

In some embodiments, the obtaining a signal line of the reference image without inversion recovery may include determining a projection curve along a readout direction of a slice, the slice providing at least one signal of the object, a peak of the projection curve corresponding to a $y_0^{th}$ line in a phase encoding direction of the real part image; and determining the signal line $L(x,y_0)$ of the reference image without inversion recovery corresponding to the $y_0^{th}$ line in the phase encoding direction of the real part image.

In some embodiments, the determining a projection curve along a readout direction of a slice that provides at least one signal of the object may include acquiring a zero phase encoding line by designating the phase encoding direction of the real part image as the readout direction of the signal line of the reference image; and determining the projection curve along the readout direction of the slice that provides at least one signal of the object by performing a one-dimensional Fourier transform on the zero phase encoding line.

In some embodiments, the projection curve along the readout direction of the slice that provides at least one signal of the object may be a projection curve along the readout direction of a middle slice of the object.

In some embodiments, a phase-corrected signal line $\hat{L}(x,y_0)$ of the reference image may be generated by performing a phase correction on the signal line $L(x,y_0)$ of the reference image.

In some embodiments, the signal line $L(x,y_0)$ of the reference image may correspond to an inversion recovery image line $S(x,y_0)$, the phase-corrected signal line $\hat{L}(x,y_0)$ of the reference image may correspond to a phased-corrected inversion recovery image line $\hat{S}(x,y_0)$, $\varphi(x,y_0)$=phase $(\hat{S}(x,y_0)*conj(S(x,y_0)))$, $\varphi(x,y_0)$ may represent a corrected phase, conj may represent an operation of determining a conjugate value, phase may represent an operation of determining a phase, and $\hat{L}(x,y_0)=L(x,y_0)*exp(1i*\varphi(x,y_0))$.

In some embodiments, the polarity of the real part image may be determined by determining whether a sum of real parts of the phase-corrected signal line $\hat{L}(x,y_0)$ of the reference image is positive or negative.

In some embodiments, the method may further include: in response to a determination that the sum of the real parts of the phase-corrected signal line $\hat{L}(x,y_0)$ of the reference image is positive, determining the polarity of the real part image to be correct; and in response to a determination that the sum of the real parts of the phase-corrected signal line $\hat{L}(x,y_0)$ of the reference image is negative, determining the polarity of the real part image to be incorrect and inversing the polarity of the real part image.

According to another aspect of the present disclosure, a method for magnetic resonance imaging is provided. The method may include generating an inversion recovery image by scanning an object using an inversion recovery sequence. The method may also include generating a real part image corresponding to the inversion recovery image by processing the inversion recovery image. The method may also include determining a signal surface or a signal body of a reference image without inversion recovery, the reference image corresponding to the real part image. The method may also include determining a phase-corrected signal surface of the reference image or a phase-corrected signal body of the reference image by performing a phase correction on the signal surface of the reference image or the signal body of the reference image. The method may also include determining a polarity of the real part image by determining whether a sum of real parts of the phase-corrected signal surface of the reference image is positive or negative, or whether a sum of real parts of the phase-corrected signal body of the reference image is positive or negative.

Compared to prior art, the method for magnetic resonance imaging provided in the present disclosure may solve the problem of inaccuracy determination of signal polarities of different tissues in a real part image in the magnetic resonance imaging (MRI) technology using an inversion recovery (IR) sequence. The polarity of a real part image may be determined by specially acquiring a signal line of a reference image and determining whether a sum of the real parts of the signal line of the reference image is positive or negative. No assumption regarding an image and a scan parameter is needed in the method for magnetic resonance imaging described in the present disclosure. The method for magnetic resonance imaging described in the present disclosure may determine polarities of real part images of all tissues accurately and reliably.

DETAILED DESCRIPTION

In the following detailed description, numerous specific details are set forth by way of examples in order to provide a thorough understanding of the disclosure. However, for persons having ordinary skills in the art, various variations and modifications may be conducted under the teaching of the present disclosure. The numerous specific details are not intended to limit the scope of the present disclosure. In addition, diagrams are used in the present disclosure for a detailed description. The diagrams are provided merely for illustration, and not intended to limit the scope of the present disclosure.

The real part imaging using an IR sequence may provide a wider contrast dynamic range and effectively increase the contrast of different tissues. However, polarities (e.g., also referred to as signs of longitudinal magnetization vectors) of different tissues may be different in the real part imaging. Thus, the polarities of different tissues may be determined using a certain technique. For example, the polarities of different tissues may be determined through an IR image or an algorithm. In prior art, the determination of the polarities through an IR image and an algorithm may be incorrect, which may lead to inconsistency between the determined polarities of the tissues and the actual polarities of the tissues, and inconsistency of contrast of different tissues in an image. In order to solve the above problem, the present disclosure provides methods for magnetic resonance imaging.

Figure 1:
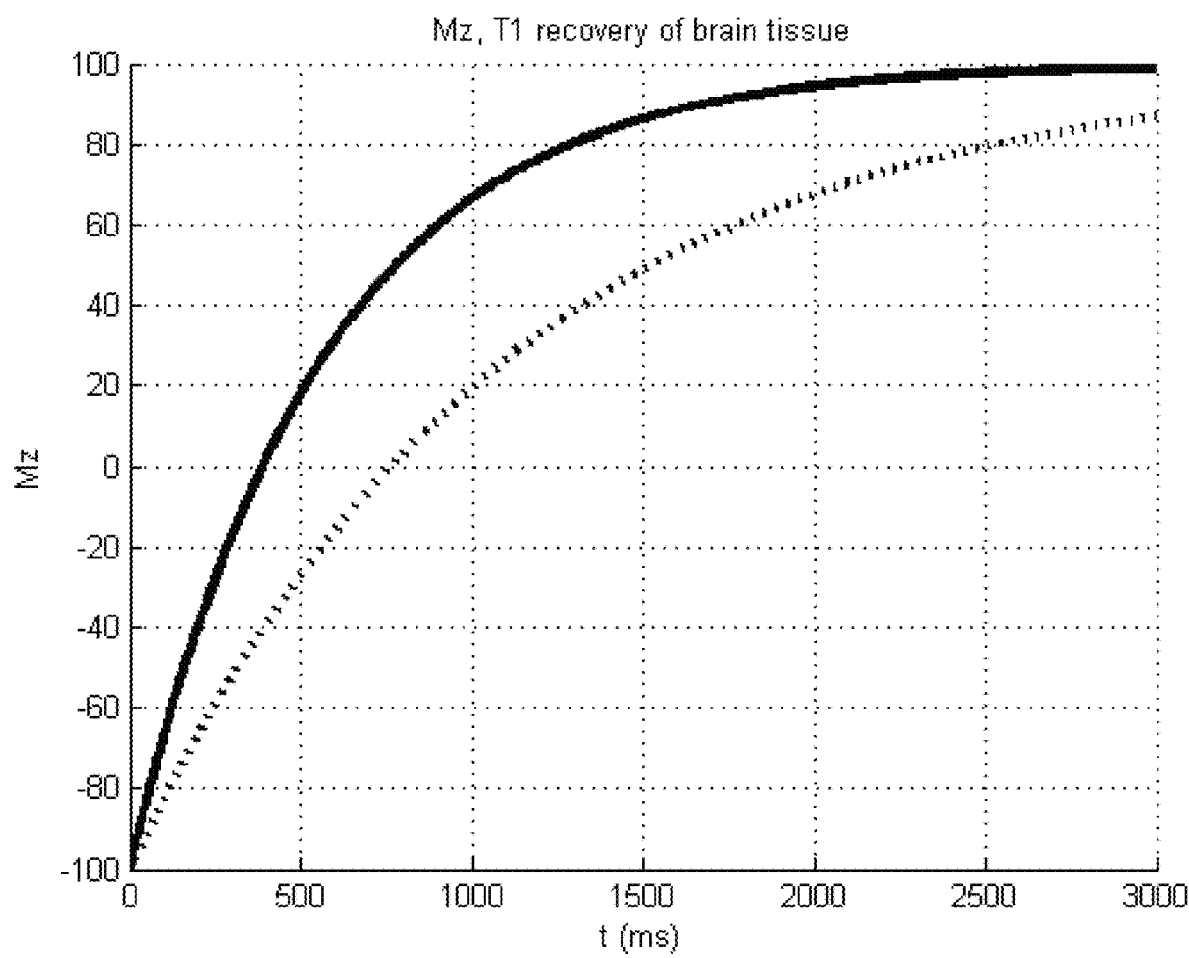
FIG. 1 is a schematic diagram illustrating exemplary inversion recovery curves of different tissues in prior art.
Figure 2:
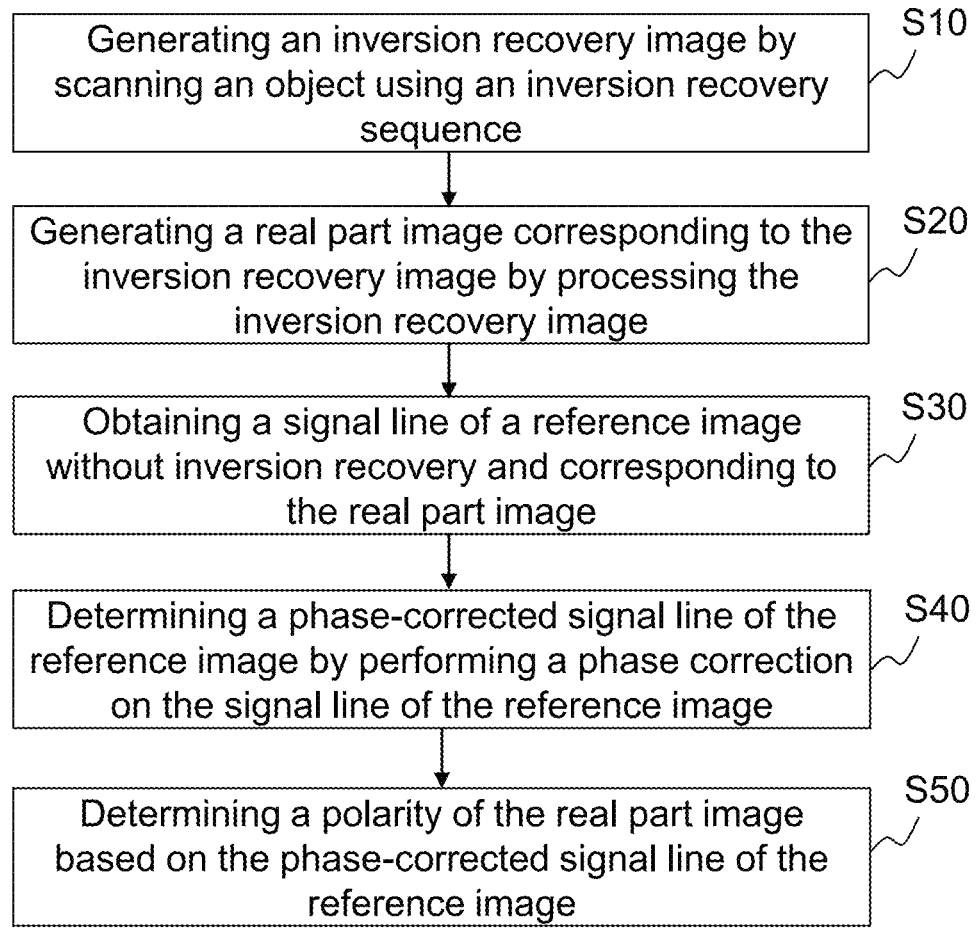
FIG. 2 is a flowchart illustrating an exemplary process for MRI according to some embodiments of the present disclosure.

As shown in FIG. 2, a method for MRI may include the following operations.

In S10, an inversion recovery image may be generated by scanning an object using an inversion recovery sequence.

In S20, a real part image corresponding to the inversion recovery image may be generated by processing the inversion recovery image.

In S30, a signal line of a reference image without inversion recovery and corresponding to the real part image may be obtained.

In S40, a phase-corrected signal line of the reference image may be determined by performing a phase correction on the signal line of the reference image.

In S50, a polarity of the real part image may be determined based on the phase-corrected signal line of the reference image.

The above operations are described in detail according to some embodiments of the present disclosure.

In S10, an inversion recovery image may be generated by scanning an object using an inversion recovery sequence.

Figure 3:
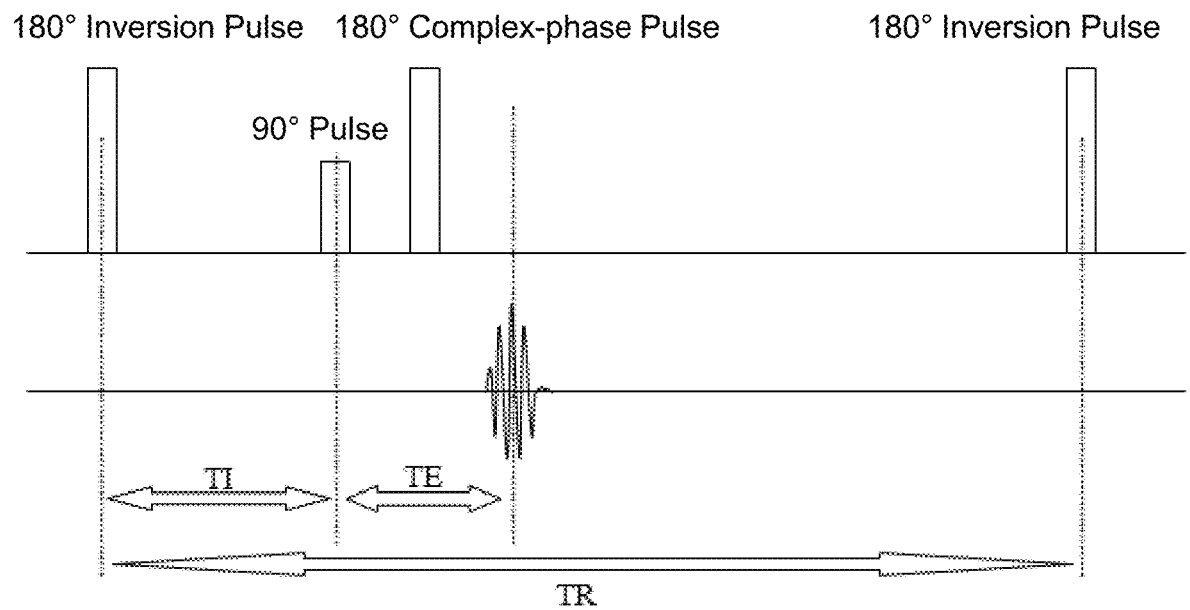
FIG. 3 is a schematic diagram illustrating an exemplary inversion recovery sequence according to some embodiments of the present disclosure.

As described in BACKGROUND, an IR sequence may include a 180° inversion pulse (e.g., also referred to as a 180° inversion pre-pulse). As shown in FIG. 3, a 180° inversion pre-pulse may be performed on the scanned tissue of the object at first. The macroscopic longitudinal relaxation vector of the scanned tissue may deflect 180°. At an appropriate time point, a 90° pulse may be performed on the scanned tissue. After the 90° pulse, a 180° complex-phase pulse may be performed on the scanned tissue and a spin echo may be acquired. As used herein, the time interval between the middle point of the 180° inversion pulse and the middle point of the 90° pulse may be referred to as an inversion time TI. The time interval between the middle point of the 90° pulse and the middle point of the spin echo may be referred to as an echo time (TE). The time interval between the middle points of two successive 180° inversion pre-pulses may be referred to as a repetition time (TR).

In S20, a real part image corresponding to the inversion recovery image may be generated by processing the inversion recovery image. Phase information of each pixel in the IR image $S(x,y)$ may include not only the polarity of the tissue, but also an error phase caused by a variety of factors including a change of a main magnetic field, a B1 field, an eddy current, a gradient delay, a motion, or the like, or a combination thereof. Thus, a phase-corrected IR image $\hat{S}(x,y)$ may be generated by performing a phase correction on the IR image $S(x,y)$. A real part image $\hat{S}_R(x,y)$ may be generated by determining real parts of the phase-corrected IR image.

In S30, a signal line of a reference image without inversion recovery and corresponding to the real part image may be determined.

The signal line of the reference image without inversion recovery may be determined before or after the real part image is generated.

Figure 4:
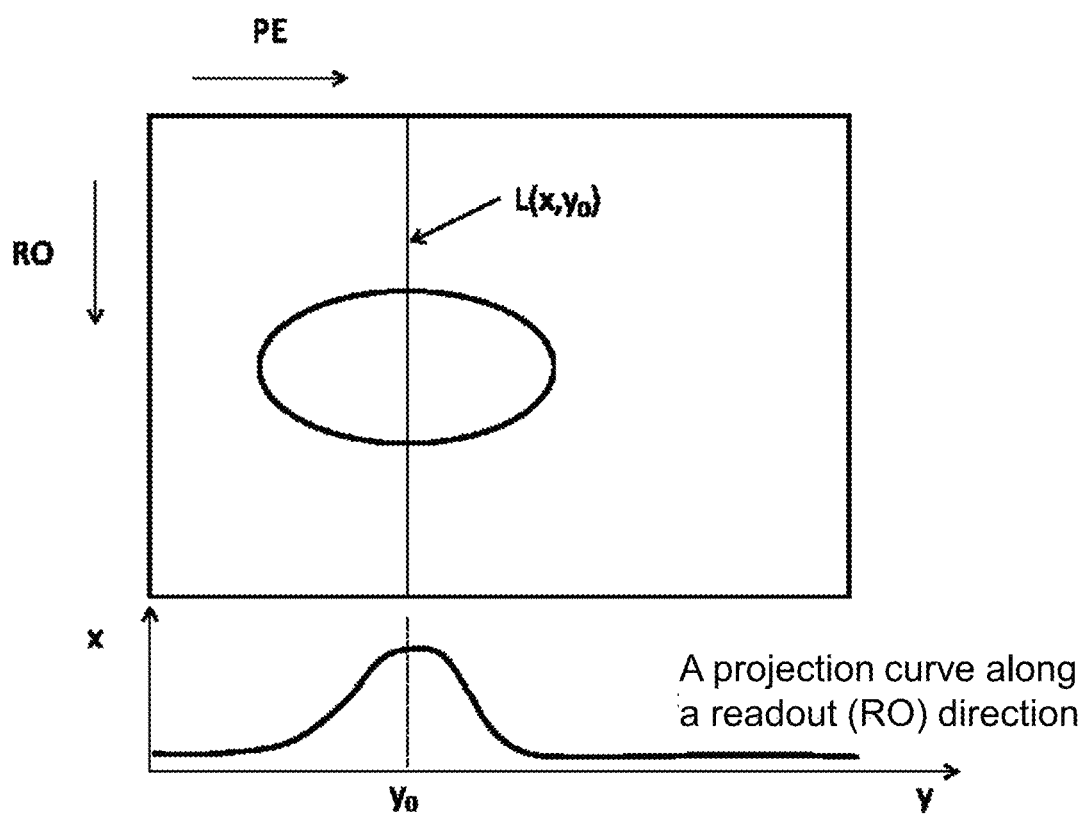
FIG. 4 is a schematic diagram illustrating an exemplary signal line of a reference image according to some embodiments of the present disclosure.

A projection curve along a readout direction of a slice that provides at least one signal of the scanned object may be determined at first. In one embodiment, a projection curve along a readout direction of a middle slice of the scanned object may be determined. The middle slice of the scanned object may always include at least one signal in a regular magnetic resonance scan. As shown in FIG. 4, a zero phase encoding line may be acquired by designating the phase encoding direction of the real part image as the readout direction of the signal line of the reference image. The zero phase encoding line may refer to a phase encoding line acquired when the phase encoding gradient is zero. The projection curve along the readout direction of the slice of the object may be determined by performing a one-dimensional Fourier transform on the zero phase encoding line and determining the amplitude of the zero phase encoding line. The peak of the projection curve may correspond to a $y_0{}^{th}$ line in the phase encoding direction of the real part image. The signal line $L(x,y_0)$ of the reference image without inversion recovery corresponding to the $y_0{}^{th}$ line in the phase encoding direction of the real part image may be determined.

In another embodiment, a projection curve along a phase encoding direction of a middle slice of the scanned object may be determined. A zero phase encoding line may be acquired by designating the phase encoding direction of the real part image as the readout direction of the signal line of the reference image. The projection curve along the readout direction of the slice of the object may be determined by performing a one-dimensional Fourier transform on the zero phase encoding line and determining the amplitude of the zero phase encoding line.

In S40, a phase-corrected signal line of the reference image may be determined by performing a phase correction on the signal line of the reference image.

The phase-corrected signal line of the reference image may be represented by $\hat{L}(x,y_0)$. An inversion recovery image line corresponding to the signal line $L(x,y_0)$ of the reference image may be represented by $S(x,y_0)$. A phase-corrected inversion recovery image line corresponding to the phase-corrected signal line $\hat{L}(x,y_0)$ of the reference image may be represented by $\hat{S}(x,y_0)$.

A corrected phase may be represented by $\varphi(x,y_0)$. $\varphi(x,y_0)$ may be determined based on the equation below:

$$\varphi(x,y_0)=\text{phase}(\hat{S}(x,y_0)*\text{conj}(S(x,y_0))),$$

where conj represents an operation of determining a conjugate value, and phase represents an operation of determining a phase.

The phase-corrected signal line $\hat{L}(x,y_0)$ of the reference image may be determined based on the equation below:

$$\hat{L}(x,y_0)=L(x,y_0)*\exp(1i*\varphi(x,y_0)).$$

In S50, a polarity of the real part image may be determined based on the phase-corrected signal line of the reference image.

In one embodiment, the polarity of the real part image may be determined by determining whether a sum of real parts of the phase-corrected signal line $\hat{L}(x,y_0)$ of the reference image is positive or negative. The polarity of the real part image may be determined based on the equation below:

$$\hat{S}_R(x,y) = \begin{cases} \hat{S}_R(x,y), \text{ if Real}\left(\sum_x \hat{L}(x,y_0)\right) > 0 \\ -\hat{S}_R(x,y), \text{ if Real}\left(\sum_x \hat{L}(x,y_0)\right) < 0 \end{cases}.$$

The polarity of the real part image may be determined to be correct in response to the determination that the sum of the real parts $\text{Real}(\Sigma_x \hat{L}(x,y_0))$ of the phase-corrected signal line $\hat{L}(x,y_0)$ of the reference image is positive. The polarity of the real part image may be determined to be incorrect and the polarity may be inversed in response to the determination that the sum of the real parts $\text{Real}(\Sigma_x \hat{L}(x,y_0))$ of the phase-corrected signal line $\hat{L}(x,y_0)$ of the reference image is negative.

It should be noted that the IR image $S(x,y)$, the phase-corrected IR image $\hat{S}(x,y)$, the inversion recovery image line $S(x,y_0)$, and the phase-corrected inversion recovery image line $\hat{S}(x,y_0)$ may be obtained by methods known by persons having ordinary skills in the art. The methods are not described in the present disclosure.

In some embodiments, the polarity of a real part image may be determined based on a signal surface of a reference image or a signal body of a reference image. The signal body may include a plurality of signal surfaces. The acquisition of a signal surface of a reference image may refer to the determination of all signal lines in a slice that provides at least one signal, such as a middle slice. The acquisition of a signal body of a reference image may refer to the determination of all signal lines of a plurality of slices that provide at least one signal, such as a middle slice and slices near the middle slice. This method for determining a polarity of a real part image may be performed based on a complete signal surface or a complete signal body. The operations of this method may be similar to the operations described above except that the method may omit the operation of acquiring a zero phase encoding line that is configured to determine the position of the signal line of a reference image and the operation of determining a projection curve by performing Fourier transform and determining the amplitude.

Figure 5:
FIG. 5 is a schematic diagram illustrating an exemplary real part image after polarities of tissue are determined based on the "Moment of Inertia" of an image determined based on a distribution characteristic of signals.
Figure 6:
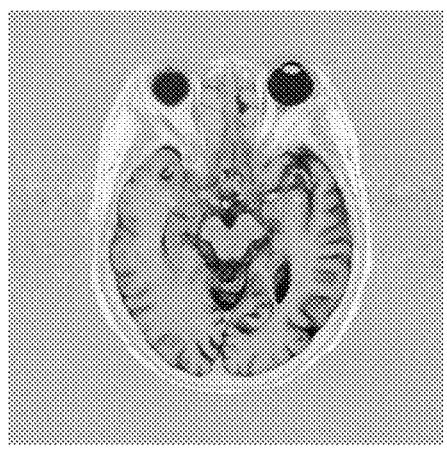
FIG. 6 is a schematic diagram illustrating an exemplary real part image after polarities of tissue are determined based on an MRI technique provided according to some embodiments of the present disclosure.

As shown in FIG. 5 and FIG. 6, FIG. 5 illustrates an example of a real part image generated by determining the polarity of the real part image based on the "Moment of Inertia" of an image that is determined based on a distribution characteristic of signals (e.g., Method 2 described in BACKGROUND). In practice, the polarities of the cerebrospinal fluid, the gray matter, and the eyeball tissue may be determined to be negative. The polarity of the scalp fat may be determined to be positive. Thus, the scalp fat area may be brighter than the other areas in a real part image, which conforms to the expected contrast consistency. The inversion recovery time in FIG. 5 is relatively short. When the scalp fat does not show sufficiently strong positive signals, the method for determining the polarity of the real part image may fail. The polarity of the real part image is inversed, which makes the scalp fat area darker than the other areas in the real part image. FIG. 6 is generated based on the same data as FIG. 5. What is different from FIG. 5 is that a method provided in the present disclosure was performed to process the data in FIG. 6. As shown in FIG. 6, the reconstructed image conforms to the expected contrast consistency when the polarity of a real part image was determined based on a specifically acquired signal line of a reference image.

Figure 7:
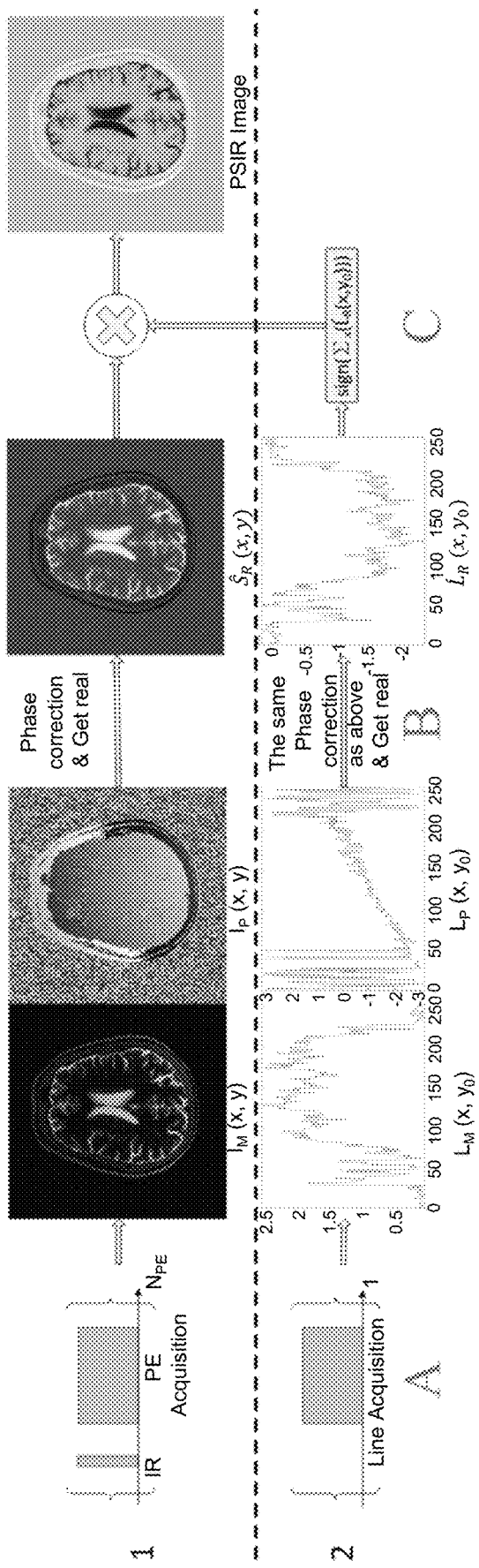
FIG. 7 is a schematic diagram illustrating an exemplary imaging process using an inversion recovery sequence according to some embodiments of the present disclosure.

FIG. 7 is a schematic diagram illustrating an exemplary imaging process based on an inversion recovery sequence according to some embodiments of the present disclosure. Stage A and stage B in process 1 may refer to operations for generating a phase-corrected real image. The operations may include generating an IR image, correcting the phase of the IR image, and generating the phase-corrected real part image by determining real parts in the phase-corrected IR image. Stage A and stage B in process 2 may refer to operations for determining a phase-corrected signal line of a reference image. The operations may include determining a signal line of a reference image, performing a phase correction on the signal line of the reference image, and determining real parts in the phase-corrected signal line. Stage A and stage B in process 2 may be performed before or after stage A and stage B in process 1. Stage C may be performed to determine the polarity of the real part image generated in process 1 using a sign of the sum of the real parts $\Sigma_x \hat{L}(x,y_0)$ (e.g., also referred to as $\Sigma_x \hat{L}_R(x,y_0)$) in the phase-corrected signal lines $\hat{L}(x,y_0)$ (e.g., also referred to as $\hat{L}_R(x,y_0)$) of the reference image determined in process 2. It should be noted that the phase-corrected signal line of the reference image in stage C may be determined by performing a phase correction on the signal line of the reference image, determining real parts in the signal line of the reference image, and determining the sum of the real parts in the signal line of the reference image. In some embodiments, the sum of the signal values $\Sigma_x \hat{L}(x,y_0)$ in the signal line $\hat{L}(x,y_0)$ of the reference image may be determined, and a real part $\text{Real}(\Sigma_x \hat{L}(x,y_0))$ of the sum of the signal values in the signal line may be determined. FIG. 7 is provided for the purpose of illustration, and not intended to limit the scope of the present disclosure.

Table 1 shows the analysis results of nine brain scans using Method 1 and Method 2 described in BACKGROUND, and a method provided in the present disclosure, respectively. For Method 1, Method 2, and the method provided in the present disclosure, a fast spin-echo inversion recovery sequence was used, and scan parameters included TR=7000 microseconds, TE=71.4 microseconds, TI=350 microseconds, ESP=10.2 microseconds, ETL=10, and 190 Hz/pixel bandwidth. As shown in Table 1, the accuracy rate of the polarity of a real part image determined according to the method provided in the present disclosure is 100%.

TABLE 1

| | A method based on a "Moment of Inertia" of an image determined according to distribution characteristic of signals (Method 2) | A method for determining a sign of a sum of real parts in a real part image based on TI (Method 1) | A method provided in the present disclosure |
|---|---|---|---|
| Correct | 5 | 2 | 9 |
| Wrong | 4 | 7 | 0 |

In real part imaging using an IR sequence, in order to solve the problem of inaccuracy in the determination of polarities of different tissues in a real part image, the present disclosure provides a method including specifically acquire a signal line of a reference image, determining a sign of a sum of real parts of the signal line, and determining a polarity of a real part image based on the sign of the sum of real parts of the signal line, without the need to assume a real part image and/or scan parameters. The method may reliably and correctly determine the polarity of a real part image relating to any tissue.

It should be noted that the above description of the present disclosure is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. And thus, the protection scope of the present disclosure should be determined based on the claims.

We claim:

1. A method for magnetic resonance imaging, the method comprising:
   generating an inversion recovery image by scanning an object using an inversion recovery sequence;
   generating a real part image corresponding to the inversion recovery image by processing the inversion recovery image;
   obtaining, without inversion recovery, a signal line of a reference image, the reference image corresponding to the real part image;
   determining a phase-corrected signal line of the reference image by performing a phase correction on the signal line of the reference image; and
   determining a polarity of the real part image based on the phase-corrected signal line of the reference image, wherein
   the signal line of the reference image corresponds to an inversion recovery image line,
   the phase-corrected signal line of the reference image corresponds to a phased-corrected inversion recovery image line,
   a corrected phase of the phase correction is determined by:

$\varphi(x, y_0) = \text{phase}(\hat{S}(x, y_0) * \text{conj}(S(x, y_0)))$, wherein $\hat{S}(x, y_0)$ representing a phase-corrected inversion recovery image line,
   $S(x, y_0)$ representing an inversion recovery image line,
   $\varphi(x, y_0)$ representing the corrected phase,
   conj representing an operation of determining a conjugate value, and
   phase representing an operation of determining a phase, and the phase-corrected signal line of the reference image is determined by $\hat{L}(x, y_0) = L(x, y_0) * \exp(1i * \varphi(x, y_0))$, $\hat{L}(x, y_0)$ representing the phase-corrected signal line of the reference image, and $L(x, y_0)$ representing the signal line of the reference image.

2. The method of claim 1, wherein the signal line of the reference image is obtained before or after the real part image is generated.

3. The method of claim 1, wherein the polarity of the real part image is determined by determining whether a sum of real parts of the phase-corrected signal line of the reference image is positive or negative.

4. The method of claim 3, further comprising:
   in response to a determination that the sum of the real parts of the phase-corrected signal line of the reference image is positive, determining that the polarity of the real part image is correct; and
   in response to a determination that the sum of the real parts of the phase-corrected signal line of the reference image is negative, determining that the polarity of the real part image is incorrect and inversing the polarity of the real part image.

5. The method of claim 1, wherein the step of generating the real part image corresponding to the inversion recovery image comprises:
   generating a phase-corrected inversion recovery image by performing a phase correction on the inversion recovery image; and
   generating the real part image corresponding to the inversion recovery image by determining real parts of the phase-corrected inversion recovery image.

6. The method of claim 1, wherein the step of obtaining the signal line of the reference image comprises:
   determining a projection curve along a readout direction of a slice;
   determining a $y_0^{th}$ line in a phase encoding direction of the real part image based on the projection curve, wherein a peak of the projection curve corresponds to the $y_0^{th}$ line in the phase encoding direction of the real part image; and
   determining the signal line of the reference image corresponding to the $y_0^{th}$ line in the phase encoding direction of the real part image.

7. The method of claim 6, wherein the step of determining the projection curve along the readout direction of the slice comprises:
   acquiring a zero phase encoding line by designating the phase encoding direction of the real part image as a readout direction of the signal line of the reference image; and
   performing a one-dimensional Fourier transform on the zero phase encoding line to determine the projection curve along the readout direction of the slice.

8. The method of claim 7, wherein the projection curve along the readout direction of the slice is a projection curve along a readout direction of a middle slice of the object.

9. A system for magnetic resonance imaging, the system comprising:
   a storage device storing instructions, and
   at least one processor, when executing the instructions, the at least one processor configured to cause the system to perform operations including:
   generating an inversion recovery image by scanning an object using an inversion recovery sequence;
   generating a real part image corresponding to the inversion recovery image by processing the inversion recovery image;

obtaining, without inversion recovery, a signal line of a reference image, the reference image corresponding to the real part image;

determining a phase-corrected signal line of the reference image by performing a phase correction on the signal line of the reference image; and determining a polarity of the real part image based on the phase-corrected signal line of the reference image, wherein the signal line of the reference image corresponds to an inversion recovery image line, the phase-corrected signal line of the reference image corresponds to a phased-corrected inversion recovery image line, a corrected phase of the phase correction is determined by:

$\varphi(x,y_0) = \text{phase}(\hat{S}(x,y_0)*\text{conj}(S(x,y_0)))$, wherein $\hat{S}(x, y_0)$ representing a phase-corrected inversion recovery image line, $S(x, y_0)$ representing an inversion recovery image line, $\varphi(x,y_0)$ representing the corrected phase, conj representing an operation of determining a conjugate value, and phase representing an operation of determining a phase, and the phase-corrected signal line of the reference image is determined by $\hat{L}(x,y_0)=L(x,y_0)*\exp(1i*\varphi(x,y_0))$, $\hat{L}(x,y_0)$ representing the phase-corrected signal line of the reference image, and $L(x,y_0)$ representing the signal line of the reference image.

10. The system of claim 9, wherein the signal line of the reference image is obtained before or after the real part image is generated.

11. The system of claim 9, wherein the operation of determining the polarity of the real part image based on the phase-corrected signal line of the reference image includes:

determining whether a sum of real parts of the phase-corrected signal line of the reference image is positive or negative.

12. The system of claim 11, wherein the operation of determining the polarity of the real part image based on the phase-corrected signal line of the reference image further includes:

in response to determining that the sum of the real parts of the phase-corrected signal line of the reference image is positive, determining that the polarity of the real part image is correct; and in response to determining that the sum of the real parts of the phase-corrected signal line of the reference image is negative, determining that the polarity of the real part image is incorrect and reversing the polarity of the real part image.

13. The system of claim 9, wherein the operation of obtaining the signal line of the reference image comprises:

determining a projection curve along a readout direction of a slice;

determining a $y_0^{th}$ line in a phase encoding direction of the real part image based on the projection curve, wherein a peak of the projection curve corresponds to the $y_0^{th}$ line in the phase encoding direction of the real part image; and determining the signal line of the reference image corresponding to the $y_0^{th}$ line in the phase encoding direction of the real part image.

14. The system of claim 13, wherein the operation of determining the projection curve along the readout direction of the slice includes:

acquiring a zero phase encoding line by designating the phase encoding direction of the real part image as a readout direction of the signal line of the reference image; and performing a one-dimensional Fourier transform on the zero phase encoding line to determine the projection curve along the readout direction of the slice.

15. The system of claim 14, wherein the projection curve along the readout direction of the slice is a projection curve along a readout direction of a middle slice of the object.

* * * * *